US010077110B2

(12) United States Patent
Erickson et al.

(10) Patent No.: US 10,077,110 B2
(45) Date of Patent: Sep. 18, 2018

(54) MONITORING FOR MOVEMENT DISORDERS USING UNMANNED AERIAL VEHICLES

(71) Applicant: International Business Machines Corporation, Armonk, NY (US)

(72) Inventors: Thomas D. Erickson, Minneapolis, MN (US); Michael S. Gordon, Yorktown Heights, NY (US); Clifford A. Pickover, Yorktown Heights, NY (US); Maja Vukovic, New York, NY (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 164 days.

(21) Appl. No.: 15/157,690

(22) Filed: May 18, 2016

(65) Prior Publication Data

US 2017/0334558 A1    Nov. 23, 2017

(51) Int. Cl.
| | | |
|---|---|---|
| *G01C 23/00* | (2006.01) | |
| *G05D 1/00* | (2006.01) | |
| *G05D 3/00* | (2006.01) | |
| *B64C 39/02* | (2006.01) | |
| *G05D 1/10* | (2006.01) | |
| *A61B 5/11* | (2006.01) | |
| *A61B 5/00* | (2006.01) | |

(52) U.S. Cl.
CPC .......... *B64C 39/024* (2013.01); *A61B 5/1101* (2013.01); *A61B 5/6887* (2013.01);
(Continued)

(58) Field of Classification Search
CPC ...... B64C 39/024; A61B 5/1101; G05D 1/101
(Continued)

(56) References Cited

U.S. PATENT DOCUMENTS

| 5,293,879 A | 3/1994 | Vonk et al. |
| 7,403,820 B2 * | 7/2008 | DiLorenzo ........... A61N 1/3605 607/45 |

(Continued)

FOREIGN PATENT DOCUMENTS

| CN | 203388861 U | 1/2014 |
| CN | 104127187 A | 11/2014 |
| GB | 2491396 A | 12/2012 |

OTHER PUBLICATIONS

Anagha Jamthe, et al; "An Implementation of Wireless Sensor Network in Monitoring of Parkinson's Patients Using Received Signal Strength Indicator"; 2013 IEEE International Conference on 2013, pp. 442-447.

(Continued)

*Primary Examiner* — Isaac G Smith
(74) *Attorney, Agent, or Firm* — Cantor Colburn LLP; Rahan Uddin

(57) ABSTRACT

Aspects include methods, systems and computer program products for evaluating a patient for a movement disorder. The method comprises defining a patient to be evaluated and deploying a unmanned aerial vehicle (UAV) to a location of the patient. The UAV includes a patient evaluation feature and at least one sensor operably coupled to the patient evaluation feature. The UAV is positioned relative to the patient to measure a patient motor characteristic. The patient motor characteristic is measured with the at least one sensor. A movement disorder is determined based at least in part on the measured patient motor characteristic. A signal is transmitted based on the detecting the movement disorder.

20 Claims, 8 Drawing Sheets

(52) U.S. Cl.
CPC ...... *G05D 1/101* (2013.01); *A61B 2562/0219* (2013.01); *B64C 2201/12* (2013.01); *B64C 2201/141* (2013.01)

(58) Field of Classification Search
USPC .......................................................... 701/3
See application file for complete search history.

(56) References Cited

U.S. PATENT DOCUMENTS

| | | | |
|---|---|---|---|
| 8,920,345 | B2 | 12/2014 | Greenberg et al. |
| 8,948,935 | B1 * | 2/2015 | Peeters ................. B64C 39/024 701/3 |
| 2002/0045952 | A1 | 4/2002 | Blemel |
| 2007/0255122 | A1 * | 11/2007 | Vol ..................... A61B 5/02125 600/301 |
| 2014/0139616 | A1 * | 5/2014 | Pinter .................. A61B 5/0008 348/14.08 |
| 2015/0158587 | A1 | 6/2015 | Patrick et al. |

OTHER PUBLICATIONS

Thomas Frey; "192 Future Uses for Flying Drones"; Business Trends, Future Scenarios, Predictions, Social Trends, Technology Trends Sep. 2, 2014; pp. 1-29; http://www.futuristspeaker.com/2014/09/192-future-uses-for-flying-drones/.

* cited by examiner

MONITORING FOR MOVEMENT DISORDERS USING UNMANNED AERIAL VEHICLES

BACKGROUND

The present invention relates generally to systems, methods and computer program products for monitoring a person using an unmanned aerial vehicle and, more specifically, to systems, methods and computer program products for using unmanned aerial vehicles for monitoring a movement disorder condition of a person or persons.

Movement disorders are a broad category of disorders or syndromes that impact the health of a patient. These disorders, which include Parkinson's disease, Wilson's disease and peripheral neuropathy, for example, are neurologic syndromes in which either the patient exhibits an excess of movement or a paucity of voluntary and automatic movements, unrelated to weakness or spasticity. Other types of disorders in this category include multiple sclerosis, chronic alcoholism, cerebellar damage, strokes and dementia with Lewy bodies (Alzheimer's disease). Tracking and monitoring of these diseases tend to occur during visits by a patient to a physician. As a result, progression of the disease is determined on a sporadic basis.

SUMMARY

Embodiments include a method, system and computer program product for evaluating a person for a movement disorder condition. The method comprises defining a patient to be evaluated and deploying a unmanned aerial vehicle (UAV) to a location of the patient. The UAV includes a patient evaluation feature and at least one sensor operably coupled to the patient evaluation feature. The UAV is positioned relative to the patient to measure a patient motor characteristic. The patient motor characteristic is measured with the at least one sensor. A movement disorder is determined based at least in part on the measured patient motor characteristic. A signal is transmitted based on the detecting the movement disorder.

Additional features are realized through the techniques of the present invention. Other embodiments and aspects of the invention are described in detail herein and are considered a part of the claimed invention. For a better understanding of the invention with the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing and other features of embodiments of the invention are apparent from the following detailed description taken in conjunction with the accompanying drawings in which:

DETAILED DESCRIPTION

Embodiments of the present disclosure are directed to systems, methods and computer program products for monitoring and evaluating a person and detecting a movement order condition, such as Parkinson's disease. Embodiments of the present disclosure utilize an unmanned autonomous vehicle ("UAV") to monitor and evaluate motor characteristics of a patient. Embodiments of the present invention further provide for monitoring of a patient using noncontact and contact based sensors on a periodic or aperiodic basis for detecting or monitoring the progression of a movement disorder.

Figure 1:
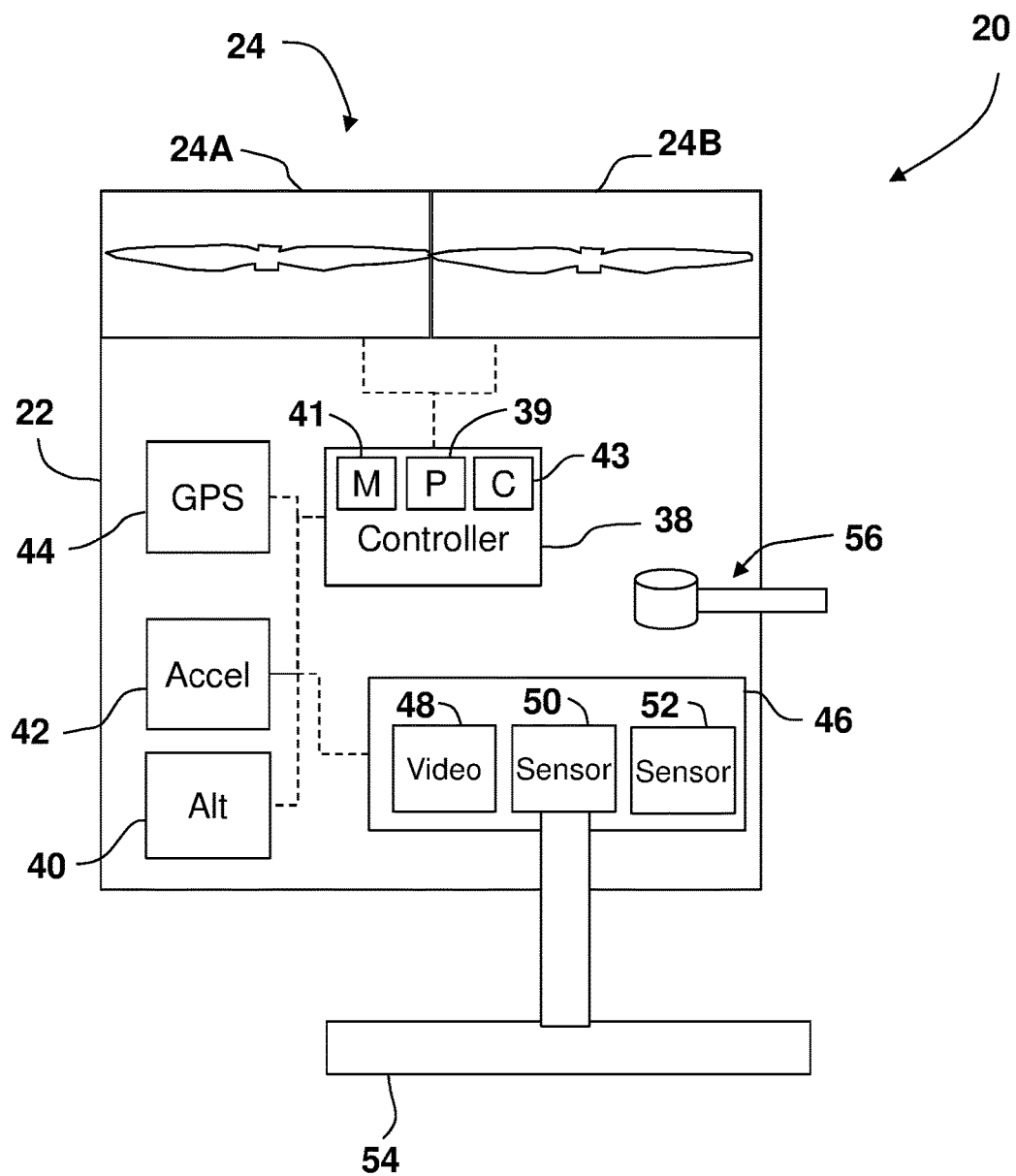
FIG. 1 depicts a block diagram of an unmanned aerial vehicle in accordance with one or more embodiments of this disclosure.

Referring now to FIG. 1, an embodiment is shown of a UAV 20. As used herein, the terms UAV or "drone" refer to an aerial vehicle capable to operating autonomously from a human operator to perform a predetermined function, such as perform monitoring functions for example. The UAV 20 includes a fuselage 22 that supports at least one thrust device 24. In one or more embodiments, the UAV 20 includes a plurality of thrust devices 24A, 24B, such as four thrust devices arranged about the periphery of the fuselage 22. In one or more embodiments, the thrust devices 24 include propeller member connected to a motor, either electric or internal combustion, which rotates to produce thrust. The thrust devices 24 may be configurable to provide both lift (vertical thrust) and lateral thrust (horizontal thrust). The vertical and horizontal components of the thrust allow the changing of the altitude (i.e. height), orientation and position of the UAV 20. In some embodiments, the orientation of the UAV 20 is with respect to the direction in which the UAV 20 pointing, with the feature 54 being the "front" or patient facing side of the UAV 20.

The UAV 20 includes a controller 38 having a processing circuit. The controller 38 may include processors that are responsive to operation control methods embodied in application code. These methods are embodied in computer instructions written to be executed by the processor, such as in the form of software. The controller 38 may further include additional circuits, such as but not limited to one or more processors 39, memory circuits 41 and communications circuits 43 for example. The communications circuit may be via a wireless communications medium. The wireless communications medium may include WiFi (e.g. IEEE 802.11), a Bluetooth® (e.g. IEEE 802.15.1 and its successors), RFID, near field communications (NFC), or cellular (e.g. LTE, GSM, EDGE, UMTS, HSPA and 3GPP cellular network technologies) for example.

The controller 38 is coupled to transmit and receive signals from the thrust devices 24 to determine and change their operational states (e.g. adjust lift from thrust devices 24, change the altitude, orientation and position of the UAV 20). The controller 38 may further be coupled to one or more sensor devices that enable to the controller to determine the altitude, orientation and position of the UAV 20. In one or more embodiments, these sensors may include an altimeter 40, a gyroscope or accelerometers 42 or a global positioning satellite (GPS) system 44. The controller 38 may use these input to operate the thrust devices 24 to move the UAV 20 to a predetermined altitude, orientation and position, and to maintain the UAV 20 in that altitude, orientation and position.

The UAV 20 may further include a patient sensor 46 that is used for monitoring the subject person. The patient sensor 46 may include a plurality of sensors, such as a video camera 48, an accelerometer 50 and a force sensor or load cell 52. The patient sensors 46 may be used to determine motor characteristics associated with the subject patient. These sensors 46 may be used in cooperation with other systems, such as grasping feature 54 discussed further herein for example, to determine if the patient has a movement disorder or if a known movement disorder has progressed. The plurality of sensors that make up the patient sensor 46 may be utilized individually, sequentially in time, or concurrently in various combinations with each other (e.g., using the video 48 and the accelerometer 50 concurrently).

It should be appreciated that while embodiments herein may refer to a particular movement disorder, such as Parkinson's disease, this is for exemplary purposes and the claimed invention should not be so limited. In other embodiments, the UAV 20 may be used to monitor any movement disorder that involves one or more measurable motor characteristics, such as but not limited to Wilson's disease, peripheral neuropathy, multiple sclerosis, chronic alcoholism, cerebellar damage, stroke, dementia, dementia with Lewy bodies, Alzheimer's disease, mercury intoxication, Hallevorden-Spatz disease, chorea, dystonias, ballismus, athetosis, dyskinesia, tic disorders, Tourette's syndrome, and fasciculation for example. Further, as used herein, the term "motor characteristic" refers to a measurement, or monitoring of the movement of muscles used by a patient during the intentional performance of a specific act (e.g. walking, writing, holding hands still, moving an arm, etc.). As will be discussed in more detail herein, patients with movement disorders have impaired motor skills that result in characteristics such as tremors, bradykinesia, rigidity, postural instability, masked face, akinesia and hypokinesia for example.

As discussed in more detail herein, in one or more other embodiments, the data acquired by the by the patient sensors 46 may be used to measure or record a motor characteristic to determine if a patient has movement disorder, if a known movement disorder has progressed, or the rate of progression has changed. In one or more embodiments, the patient sensor 46 may include a distance meter, a RADAR type device, a LIDAR type device, or a SONAR type device.

In one or more embodiments, the UAV 20 includes a grasping feature 54 that is a demarcation location for the patient to grasp or hold on to the UAV 20. In the exemplary embodiment, the feature 54 is a bar, rod, ring or handle that extends from the fuselage 22 in such a manner that the patient may hold or grasp the feature 54 while the UAV 20 hovers near the patient. The feature 54 may be coupled to the sensor 50 or sensor 52. The sensor 50 which, as previously noted herein, may be implemented as a tri-axial accelerometer for example. In the illustrated embodiments, the accelerometer 50 is used to measure vibrations caused by tremors in the patient's hands. It should be appreciated that while the illustrated embodiment shows the accelerometer 50 as being located within the fuselage 22, this is for exemplary purposes and the claims should not be so limited. In one or more other embodiments, the accelerometer 50 is positioned within the grasping feature 54 and may be outside of the fuselage 22. In one or more embodiments, the grasping feature 54 extends from and retracts into the fuselage 22, thus rendering movable any patient sensors 46 connected to the grasping feature 54. Further, in one or more other embodiments, the grasping feature 54 may be in the form of a glove that the patient inserts their hand into during testing. One or more of the accelerometers 50 may be incorporated into the glove.

In one or more embodiments, the feature 54 may include additional sensors, such as a load cell 52 or a strain gage for example. These additional sensors may be used to measure characteristics, such as hand grip strength or hand torsion strength for example. In one embodiment, the feature 54 includes a portion that rotates about an axis and a restrictor device, such as a motor, that applies or resists rotation.

In one or more embodiments, the sensor 52 may include a microphone configured to record the patient's voice. The microphone may include filters to cancel or remove noise generated by the UAV 20. It has been found that soft, low or a hoarse voice by the patient may be a warning sign of Parkinson's disease.

In one or more embodiments, the UAV 20 may further include an olfactory testing device 56. The olfactory testing device 56 emits an odor to be smelled by the patient. In one embodiment, the olfactory testing device 56 simulates the University of Pennsylvania Smell Identification Test (UPSIT). It has been found that a loss of smell is an early indicator of the onset of Parkinson's disease and the testing for the loss of smell may be used as a diagnostic tool.

Figure 2:
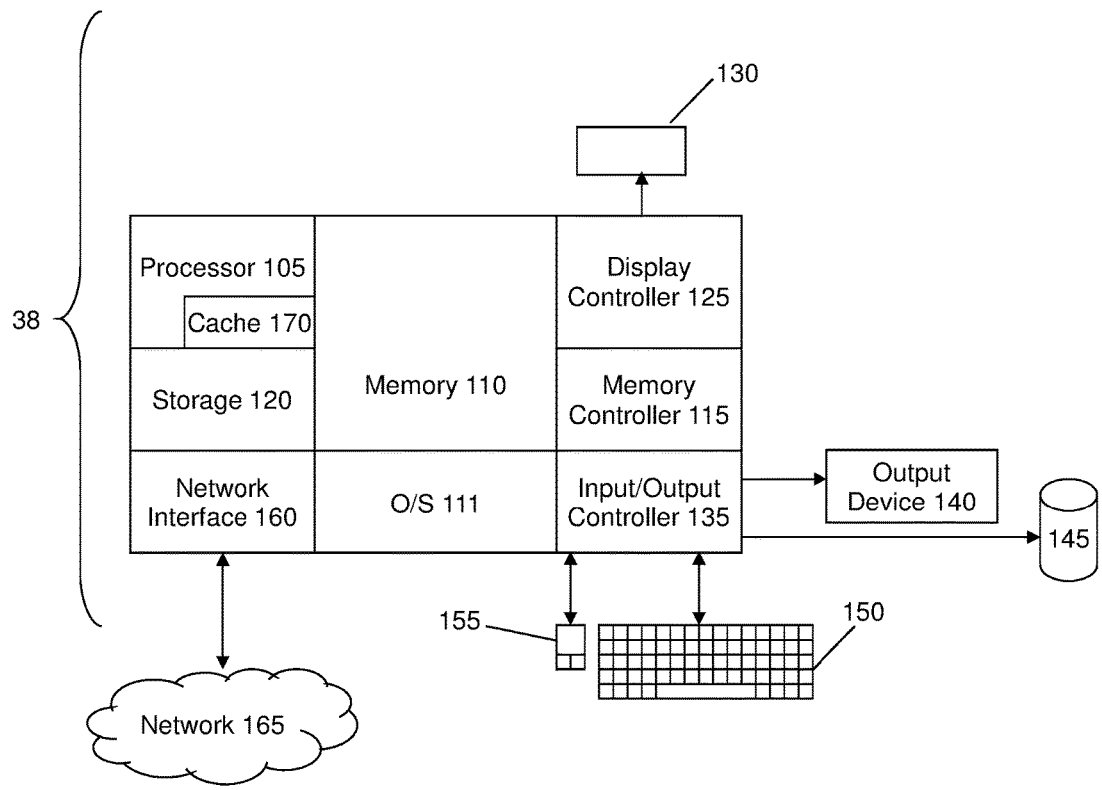
FIG. 2 depicts a block diagram of a controller for an unmanned aerial vehicle in accordance with one or more embodiments of this disclosure.

FIG. 2 illustrates a block diagram of an embodiment of controller 38 for use in implementing a system or method according to one or more embodiments. The systems and methods described herein may be implemented in hardware, software (e.g., firmware), or a combination thereof. In one or more embodiments, the methods described may be implemented, at least in part, in hardware and may be part of the microprocessor of a special or general-purpose controller, such as a personal computer, workstation, minicomputer, or mainframe computer.

In one or more embodiments, as shown in FIG. 2, the controller 38 includes a processor 105, memory 110 coupled to a memory controller 115, and one or more input devices 145 and/or output devices 140, such as peripheral or control devices that are communicatively coupled via a local I/O controller 135. These devices 140 and 145 may include, for example, battery sensors, position sensors, accelerometers, cameras, video cameras, microphones, audio speakers and the like. Input devices such as a conventional keyboard 150 and mouse 155 may be coupled to the I/O controller. The I/O controller 135 may be, for example, one or more buses or other wired or wireless connections, as are known in the art. The I/O controller 135 may have additional elements, which are omitted for simplicity, such as controllers, buffers (caches), drivers, repeaters, and receivers, to enable communications.

The I/O devices 140, 145 may further include devices that communicate both inputs and outputs, for instance disk and tape storage, a network interface card (MC) or modulator/demodulator (for accessing other files, devices, systems, or a network), a radio frequency (RF) or other transceiver, a telephonic interface, a bridge, a router, and the like.

The processor 105 is a hardware device for executing hardware instructions or software, particularly those stored in memory 110. The processor 105 may be a custom made or commercially available processor, a central processing unit (CPU), an auxiliary processor among several processors associated with the controller 38, a semiconductor based microprocessor (in the form of a microchip or chip set), a macroprocessor, or other device for executing instructions. The processor 105 includes a cache 170, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 170 may be organized as a hierarchy of more cache levels (L1, L2, etc.).

The memory 110 may include one or combinations of volatile memory elements (e.g., random access memory, RAM, such as DRAM, SRAM, SDRAM, etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 110 may incorporate electronic, magnetic, optical, or other types of storage media. Note that the memory 110 may have a distributed architecture, where various components are situated remote from one another but may be accessed by the processor 105.

The instructions in memory 110 may include one or more separate programs, each of which comprises an ordered listing of executable instructions for implementing logical functions. In the example of FIG. 2, the instructions in the memory 110 include a suitable operating system (OS) 111. The operating system 111 essentially may control the execution of other computer programs and provides scheduling, input-output control, file and data management, memory management, and communication control and related services.

Additional data, including, for example, instructions for the processor 105 or other retrievable information, may be stored in storage 120, which may be a storage device such as a hard disk drive or solid state drive. The stored instructions in memory 110 or in storage 120 may include those enabling the processor to execute one or more aspects of the systems and methods of this disclosure.

The controller 38 may further include a display controller 125 coupled to a user interface or display 130. In one or more embodiments, the display 130 may be an LCD screen. As discussed in more detail herein, the display 130 may be used for communicating with the patient, such as to provide instructions during the evaluation. In one or more embodiments, the controller 38 may further include a network interface 160 for coupling to a network 165. The network 165 may be an IP-based network for communication between the controller 38 and an external server, client and the like via a broadband connection. The network 165 transmits and receives data between the controller 38 and external systems. In one or more embodiments, the external system may be the UAV 20, wherein the transmitting and receiving of data allows the controller 38 to determine when a condition (e.g. tremor frequency). In one or more embodiments, the network 165 may be a managed IP network administered by a service provider. The network 165 may be implemented in a wireless fashion, e.g., using wireless protocols and technologies, such as WiFi, WiMax, satellite, etc. The network 165 may also be a packet-switched network such as a local area network, wide area network, metropolitan area network, the Internet, or other similar type of network environment. The network 165 may be a fixed wireless network, a wireless local area network (LAN), a wireless wide area network (WAN) a personal area network (PAN), a virtual private network (VPN), intranet or other suitable network system and may include equipment for receiving and transmitting signals.

Systems and methods according to this disclosure may be embodied, in whole or in part, in computer program products or in controller 38, such as that illustrated in FIG. 2.

Figure 3A:
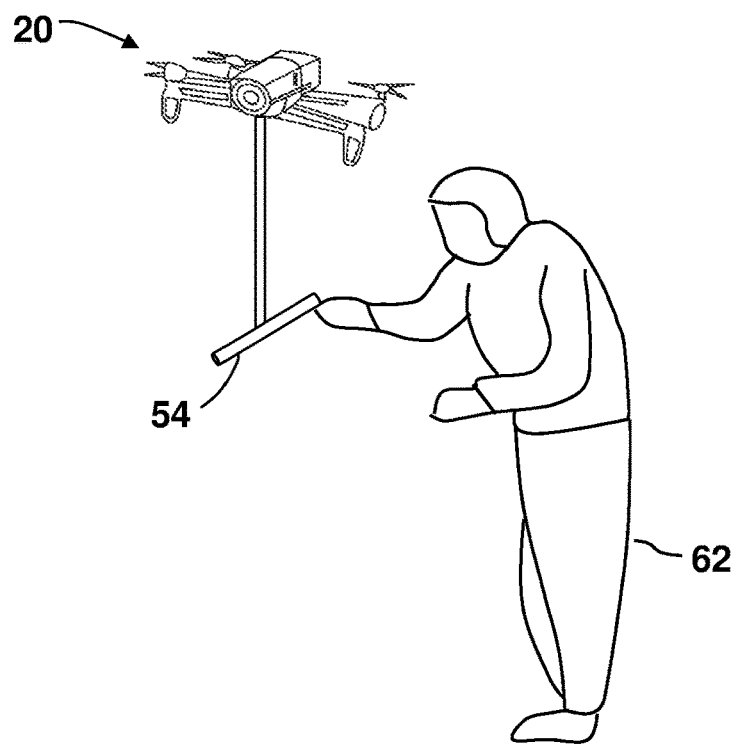
FIG. 3A and FIG. 3B depict a view of unmanned aerial vehicle performing a test on a patient in accordance with one or more embodiments of this disclosure.
Figure 3B:
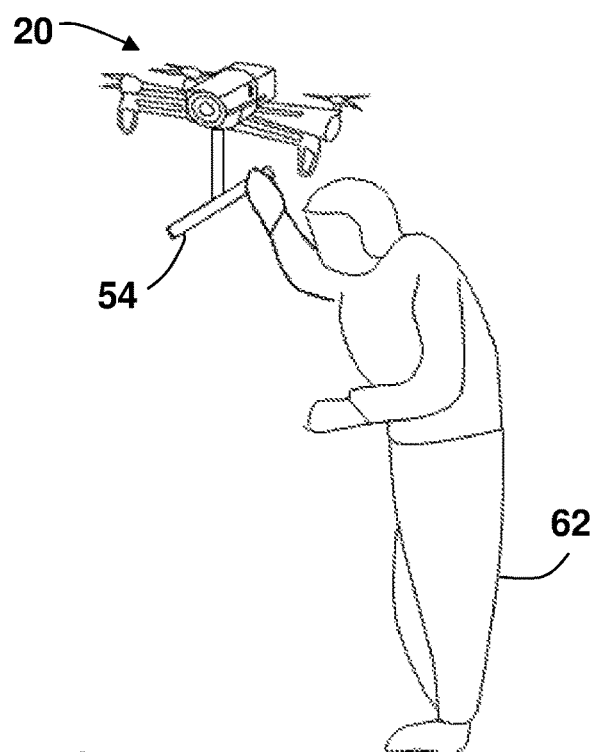
Figure 4A:
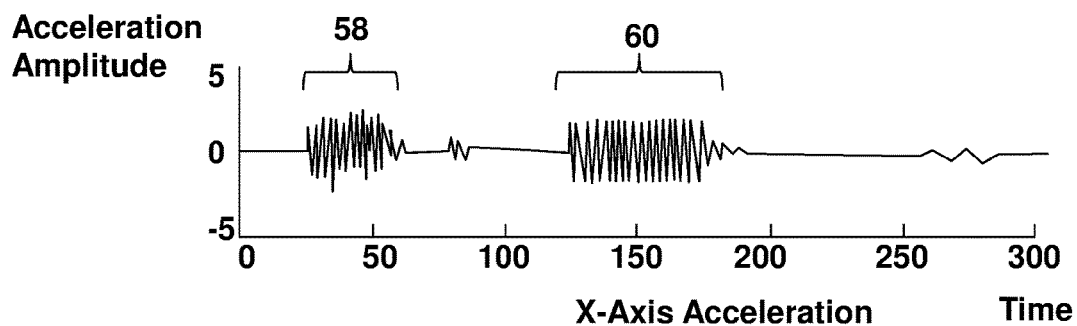
FIG. 4A, FIG. 4B and FIG. 4C depict a plot of an exemplary acceleration vs time relationship as measured by an accelerometer on an unmanned aerial vehicle.
Figure 4B:
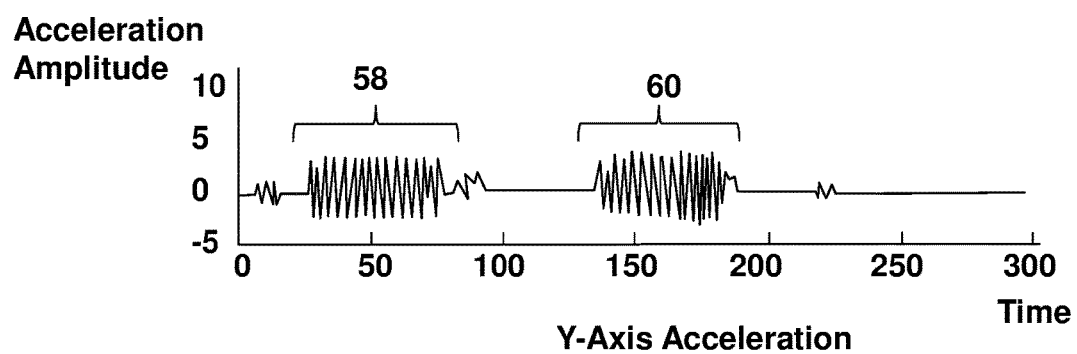
Figure 4C:
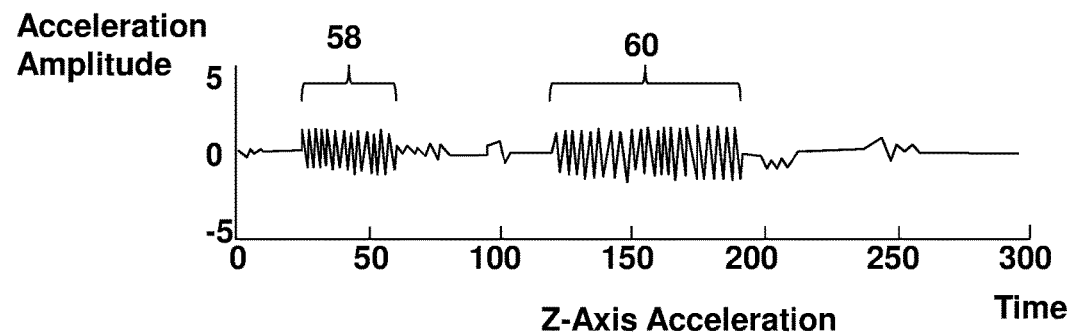

Referring now to FIG. 3A and FIG. 3B, with continuing reference to FIG. 1, an embodiment is shown for evaluating or monitoring the progression of a movement disorder in a patient using a UAV 20. One motor characteristic of a patient having a movement disorder such as Parkinson's disease is a tremor or an uncontrolled shaking of a body part, such as the patient's hand(s). In the case of Parkinson's disease, the tremor typically occurs at a frequency range of 4 Hertz (Hz) to 6 Hz when measured by an accelerometer in operable connection with the body part (e.g. hands) of the patient. An example of an accelerometer measurement is shown in FIGS. 4A-4C for each axis of a tri-axial accelerometer. It should be noted that some portions of the accelerometer output, such as portions 58, 60 exhibit a vibration/tremor with a frequency of 4-6 Hz.

In one or more embodiments, the UAV 20 with the grasping feature or bar 54 positioned adjacent the patient 62 at a desired testing height. It should be appreciated that the use of a UAV 20 to perform the tremor testing may provide advantages in allowing the bar 54 to be positioned at a predetermined height or position relative to the patient 62 body. This allows the UAV 20 to carry out testing with a variety of patients of different heights, body statures or positions (e.g. standing, sitting, or prone). In one embodiment, the UAV 20 receives patient height data prior to testing to determine the position of the bar 54. As will be discussed in more detail below, this patient data may be transmitted from a remotely located computer over a transmission medium, such as a wireless network for example. In one or more other embodiments, the UAV 20 may adapt the position of the bar 54 based on image analysis of the patient 62 upon arrival of the UAV 20 at a patient location. For example, using video camera 48, the UAV 20 may use image analysis to determine the height of the patient 62. In one or more other embodiments, the UAV 20 uses image analysis to determine the body position or orientation (e.g. the position of the arm relative to the shoulder, the amount of bending at elbow), and adjust the height of the bar 54 to the predetermined position. The UAV 20 may determine the body position of the patient 62 (e.g. standing, sitting, or prone) using the video camera 48.

The UAV 20 may further allow for testing at a variety of predetermined body positions by adjusting the position of the bar 54. For example, in FIG. 3A, the bar 54 is placed at a position below the shoulder of the patient 62 with the elbow bent, while in FIG. 3B the bar 54 is positioned above the head of the patient 62. This allows for the measurement of motor characteristics at a variety of positions by the repositioning of the UAV 20.

To monitor for tremors, the UAV 20 positions itself and the patient 62 grasps or holds the bar 54. The testing may be performed on each hand separately, or both hands together. In one or more embodiments, the UAV 20 may have an interface that allows the UAV 20 to communicate with the patient 62 to convey instructions to the patient 62 on actions to be performed. The interface may include an audio speaker, a display screen (e.g. LCD), lights (e.g. LED's) or a combination of the foregoing. The audio speaker may allow the UAV 20 to provide spoken instructions to the patient (e.g. "hold on to the bar"). The display screen may provide written instructions or graphical instructions (e.g. a picture of a person holding the bar). While the patient 62 holds the bar 54, measurements are made with accelerometer 50, the results of which are shown in FIGS. 4A-4C. In one embodiment, the accelerometer circuit may include a band pass filter to suppress signals outside of the desired frequency range, such as 4 Hz to 6 Hz for example. The filter may include a Least Squares filter, a Hamming Window bandpass filter, or a Parks-McClellan filter. In still other embodiments, the accelerometer signal may be integrated over the running intervals with the tremor being detected when the integrated signal amplitude exceeds a threshold.

The analysis of the accelerometer signal may be performed in real-time as the measurements are made, or after the testing is completed. In one or more embodiments, the measurements are performed for a predetermined period of time. Further, the analysis of the accelerometer signal may be performed by the controller 38, by a remote computer 300 located, for example, in a physician's office (FIG. 6), or by one or more nodes 452 in a distributed or cloud computer network (FIG. 7) for example. The accelerometer 50 signals (or the integrated signal) may be transmitted by controller 38 via network interface 160 for example.

In one or more embodiments, the UAV 20 may move in a predetermined manner during the tremor evaluation to measure the accelerometer signals during movement. It has been found that in some cases a tremor caused by Parkinson's disease may stop when the person begins an action.

As discussed in more detail below, in one or more embodiments when a tremor is detected, the UAV 20 may perform other predetermined tests or may monitor the patient visually via video camera 48. In one or more embodiments, the UAV 20 may utilize olfactory testing device 56 to measure the response of the patient 62 to smells.

It should be appreciated that while the embodiments herein include the evaluation of the patient 62 for tremors, this is for exemplary purposes and the claimed invention should not be so limited. In other embodiments, other motor characteristics of the patient 62 may be evaluated, such as but not limited to bradykinesia, rigidity, postural instability, masked face, akinesia and hypokinesia. Some of the evaluation testing may be performed with the assistance of medical personnel such as a nurse for example. For example, postural instability may involve the UAV 20 applying resistance against the patient 62, when the patient pushes the bar 54, with a predetermined force with the medical personnel supervising. The video camera 48 is used to monitor how patient recovers from the application of the force. Rigidity and bradykinesia testing may utilize additional sensors, such as load cell 52 for example, which when combined with a determination of the amount of thrust generated by the thrust devices 24 may determine how fast the arm moves or how much force is used to move an arm or hand.

Some of the evaluation testing may be non-contact, such as masked face testing is performed using the video camera recording the face of patient 62. Image analysis is then used in cooperation with the recorded video images to identify facial characteristics, such as but not limited to: a blank stare, infrequent blinking of eyes, serious facial expression, and depressed facial expression for example. Further, some evaluation testing may include having the patient 62 point their hand or finger at the UAV 20 and the UAV 20 moving in a predetermined pattern at a predetermined speed. The video camera 48 records the patient's hand as the UAV 20 moves through the pattern. In one or more embodiments, the UAV 20 may have a light source (e.g. LED) that the patient 62 points at during the testing.

In one or more embodiments, the UAV 20 may also be configured to evaluate degradation of memory by asking the patient questions, either audibly (via an audio speaker) or using a display and recording a response. The UAV 20 may further be configured to evaluate handwriting skills by recording the patient's writing. It should be appreciated that the motor characteristic measurements may be stored by the UAV 20, such as in memory 110 (FIG. 2) for example, or in a node 452 (FIG. 7) for example. In one or more embodiments, the node 452 may store the patient's electronic medical records (EMR). By comparing present/current motor characteristic measurements with previous measurements, changes in the patient's condition may be evaluated. In one or more embodiments, when the change in the motor characteristic measurement exceeds a threshold, the UAV 20 may transmit a signal to medical personnel, such as a physician 302 (FIG. 6) for example, to notify them of a potential change in condition.

Further, in one or more embodiments, the motor characteristic evaluation may be performed on periodic or aperiodic basis. In one or more embodiments, the motor characteristic evaluation may be performed on a frequent basis, such as daily, weekly or bi-weekly for example, between in-person visits with a treating physician. This allows the physician to more accurately monitor the progression of the disease or syndrome when compared to only testing when the patient 62 visits the physician (typically every 2-3 months).

Figure 5:
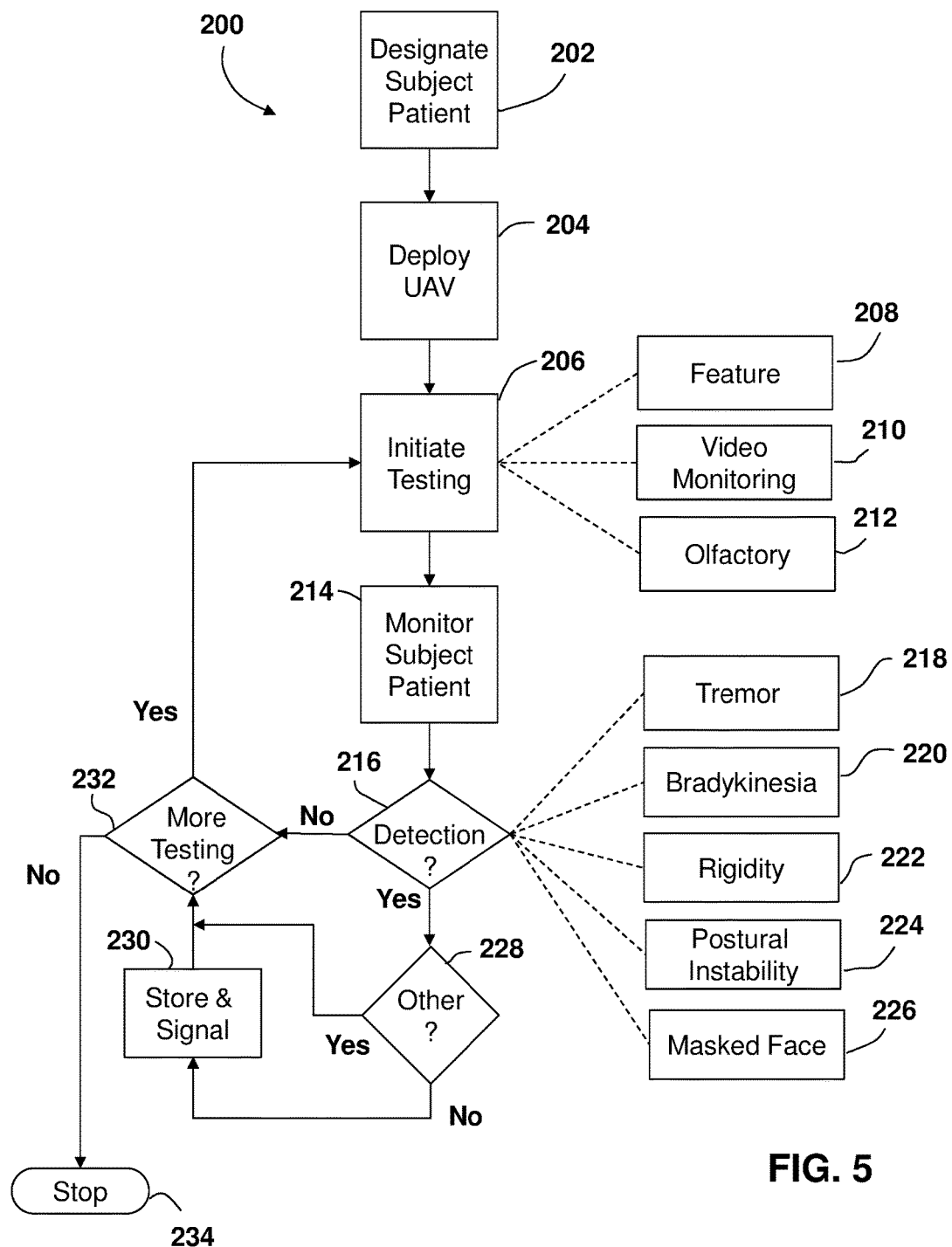
FIG. 5 depicts a flow diagram of a method of monitoring a patient for a movement disorder in accordance with one or more embodiments of this disclosure.

Referring now to FIG. 5, a method 200 is shown for evaluating the patient 62 for a movement disorder. The method 200 begins in block 202 where the patient is designated. The designation may include transferring information about the patient to the UAV 20, or enabling the UAV 20 access to some of the patient's information or data (e.g. patient's electronic medical record) on a remote computer or node. This information may include, but is not limited to the patient's physical characteristics (e.g. height), as well as patient demographics, such as location, motor characteristics to be evaluated or monitors, medical history, physical conditions, prescription pharmaceuticals being taken, and previous motor characteristic evaluation measurements for example. The UAV 20 is then deployed to the location of the patient 62 in block 204. In one or more embodiments, the patient location may be transmitted on a periodic, aperiodic or continuous basis (such as to a remote computer for example) to allow the UAV 20 to travel to the patient location. In one or more embodiments, the UAV 20 may be deployed within a medical facility, such as hospital, nursing home, or rehabilitation facility for example. In still other embodiments, the UAV 20 travels between a base location (e.g. a medical care provider) and the patient's location (e.g. the patient's home). In one or more embodiments the UAV 20 may evaluate and monitor a single patient. In other embodiments, the UAV 20 may evaluate and monitor a plurality of patients at the same or different locations.

Upon arriving at the patient's location, the UAV 20 initiates testing in block 206. In one or more embodiments, the UAV 20 may be configured to perform a variety of movement disorder evaluations. The UAV 20 may include a feature module 208 (e.g. holding of the bar 54), a video monitoring module 210, or an olfactory testing module 212 for example. The method 200 then proceeds to block 214 where the motor characteristic of the subject patient is monitored or evaluated. For example, in a tremor evaluation, the patient may hold the bar 54 and signals from an accelerometer 50 are recorded. For masked face evaluation, the patient's face may be monitored with a video camera and image analysis used to evaluate the reactions and movements of the face.

The method 200 then proceeds to query block 216 where the motor characteristic is analyzed to determine if a movement disorder may be indicated or if an existing movement disorder has progressed. In one or more embodiments, the UAV 20 may have a tremor module 218, a bradykinesia module 220, a rigidity module 222, a postural instability module 224, or masked face module 226. In some evaluations, the determination may be based on a comparison of the measured motor characteristic to a threshold. In other evaluations, the determination may be based on a difference between a current motor characteristic measurement and one or more previous measurements. In one or more embodiments using multiple previous measurements, the determination may be based on a trend of the measurements or a rate of change of the measurements.

In one or more embodiments, the UAV 20 may determine if the movement disorder was indicated based on the patient cohort, such as based on age group, location, cultural background or other medical conditions for example.

When the query block 216 returns a positive, meaning a movement disorder condition has been detected, the method 200 proceeds to query block 228 where it is determined if there are other conditions that may have caused the detection (e.g. a false positive). For example, the patient may be taking a medication that may cause similar motor characteristics to a masked face. When query block 228 returns a negative, the method 200 proceeds to block 230 where the measured or recorded motor characteristic data are stored. In one or more embodiments, the method 200 may further transmit a signal to medical personnel if the measured or recorded motor characteristic crosses a threshold value. It should be appreciated that the stored data may include multiple parameters. For example, in the embodiment where a tremor is evaluated the measured motor characteristics may include timing of the tremor occurrences, amplitude data and other activities (e.g. body positions at which measurements were taken, pharmaceuticals taken by patient, food recently eaten by patient).

Once these activities are completed in block 230, when query block 228 returns a positive, or when query block 216 returns a negative, the method 200 proceeds to block 232 where it is determined if additional testing is to be performed. When query block 232 returns a positive, the method 200 loops back to block 206 and the next test is initiated. When query block 232 returns a negative, the method 200 proceeds to block 234 and stops.

Figure 6:
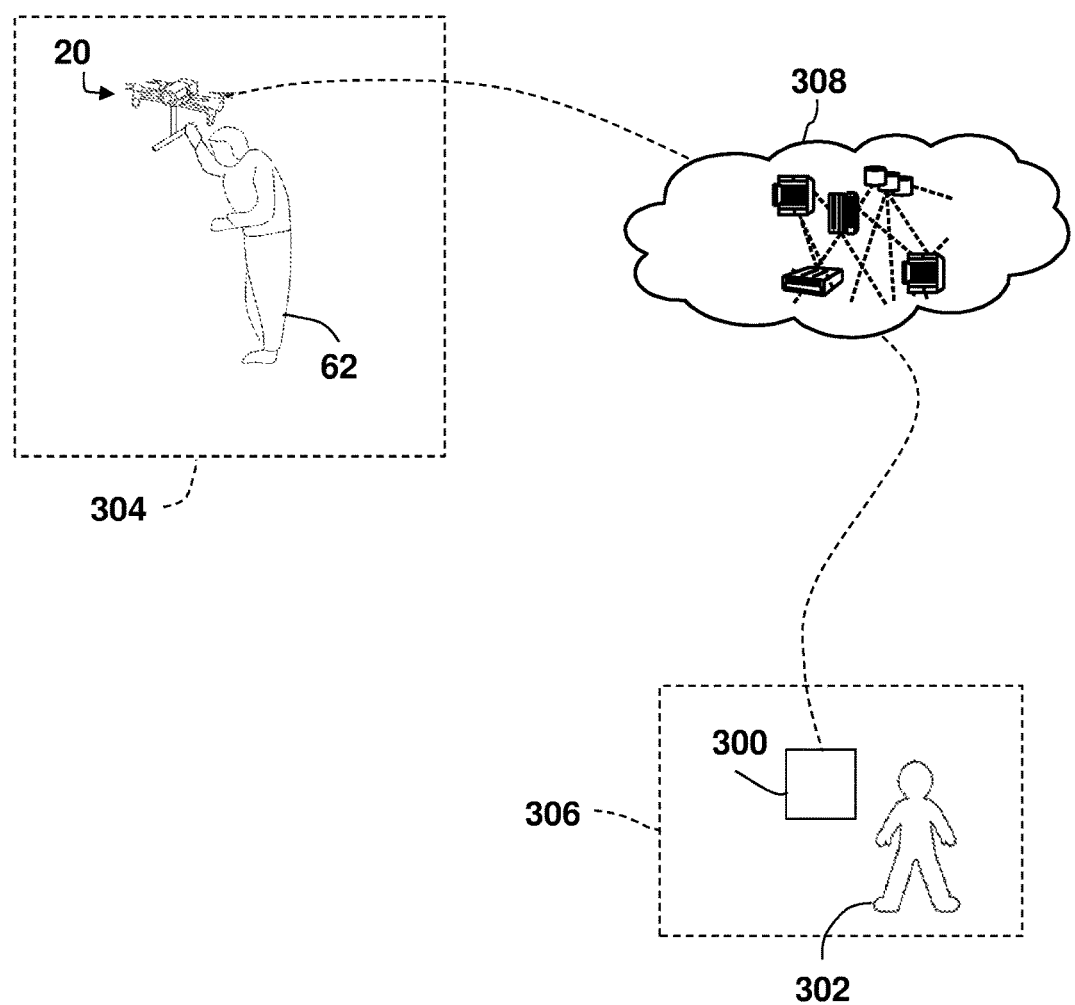
FIG. 6 depicts a schematic view of a remote examination of a patient by a doctor in accordance with one or more embodiments of this disclosure.

While the embodiments of FIGS. 3-5 described the operation of the UAV 20 acting in an autonomous manner, this is for exemplary purposes and the claimed invention should not be so limited. Referring now to FIG. 6, an embodiment is shown where the UAV 20 operates at least partially based on commands received by a medical personnel 302 (e.g. a physician). In this embodiment, it is contemplated that the patient 62 is in a first location 304 (e.g. their home) and the medical personnel 302 are in a second location 306 (e.g. medical office) where the second location 306 is remotely located from the first location 304. It should be appreciated that in one or more embodiments the patient 62 and medical personnel 302 may be located in the same but different parts of the same facility or medical campus.

In this embodiment, the UAV 20 may be connected for communication via a network 308 that allows for transmission bidirectional signals between a computer 300 operated by the medical personnel 302 and the UAV 20. The network 308 may be a LAN, a WAN, a PAN, an intranet, or the Intranet for example. The UAV 20 in response to a signal from the medical personnel 302 performs evaluation procedures and the medical personnel may see the measured motor characteristics in real time or near real-time. In one or more embodiments, the medical personnel 302 may observe the patient 62 during the evaluation via the video camera 48. In one or more embodiments, the medical personnel 302 may speak to the patient 62 via an audio speaker and microphone on the UAV 20. In this embodiment, the medical personnel 302 may change the evaluation procedure or provide different testing protocols via the UAV 20. Thus, in this embodiment, the UAV may operate in a semi-autonomous mode of operation, with the medical personnel controlling the evaluation.

In one or more embodiments, the UAV 20 may store or receive data or information from one or more remote computers. Further, some or all of the evaluation of the motor characteristic measurements may be performed on the UAV 20, or more be performed on one or more remote computers. For example, the determination of whether a movement disorder is indicated (block 216, FIG. 5) may be performed by a computing device remotely located from the UAV 20. In one embodiment, a cloud computing environment may cooperate with the UAV 20 in the evaluation and monitoring of movement disorders.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
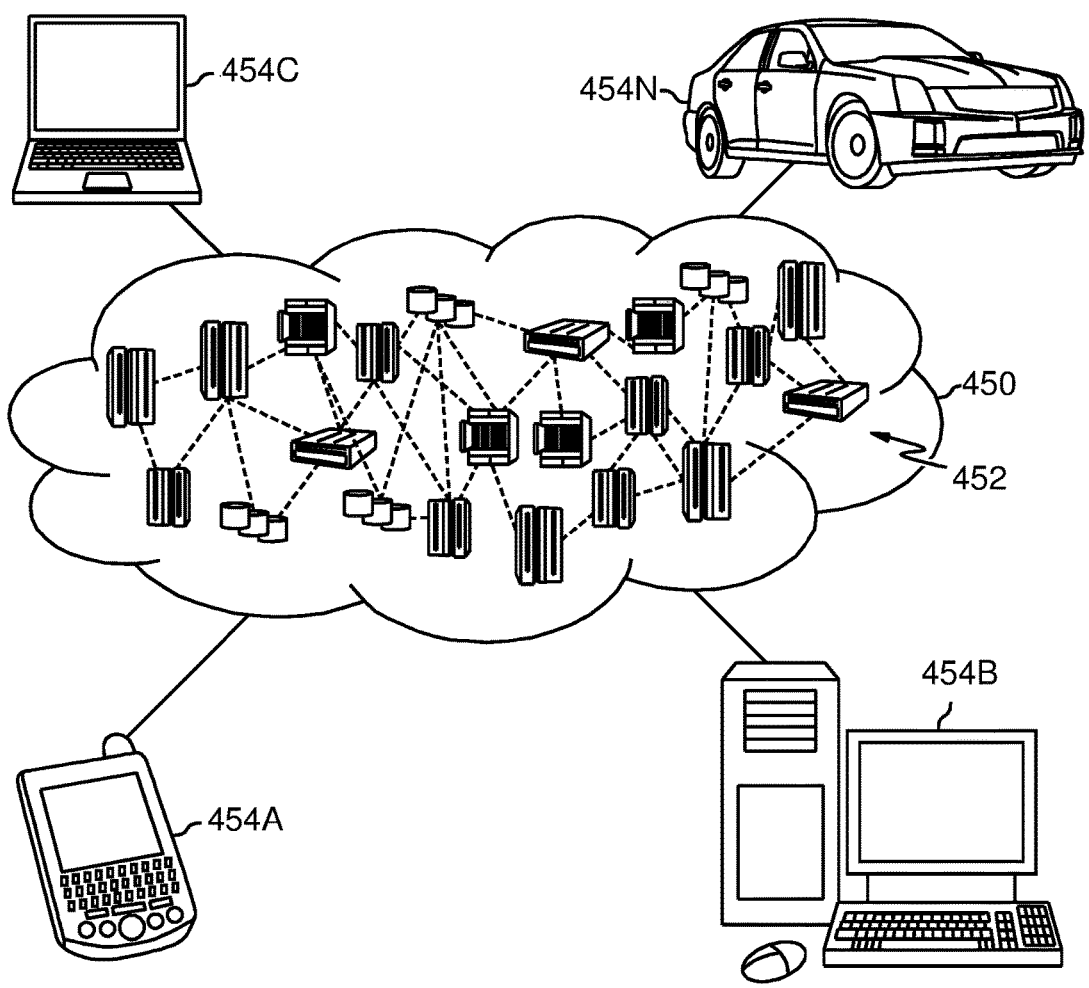
FIG. 7 depicts a cloud computing environment according to one or more embodiments of the present invention.

Referring now to FIG. 7, illustrative cloud computing environment 450 is depicted. As shown, cloud computing environment 450 comprises one or more cloud computing nodes 452 with which local computing devices used by cloud consumers, such as, for example, personal digital assistant (PDA) or cellular telephone 454A, desktop computer 454B, laptop computer 454C, and/or automobile computer system 454N may communicate. Nodes 452 may communicate with one another. They may be grouped (not shown) physically or virtually, in one or more networks, such as Private, Community, Public, or Hybrid clouds as described hereinabove, or a combination thereof. This allows cloud computing environment 450 to offer infrastructure, platforms and/or software as services for which a cloud consumer does not need to maintain resources on a local computing device. It is understood that the types of computing devices 454A-N shown in FIG. 7 are intended to be illustrative only and that computing nodes 452 and cloud computing environment 450 can communicate with any type of computerized device over any type of network and/or network addressable connection (e.g., using a web browser).

Figure 8:
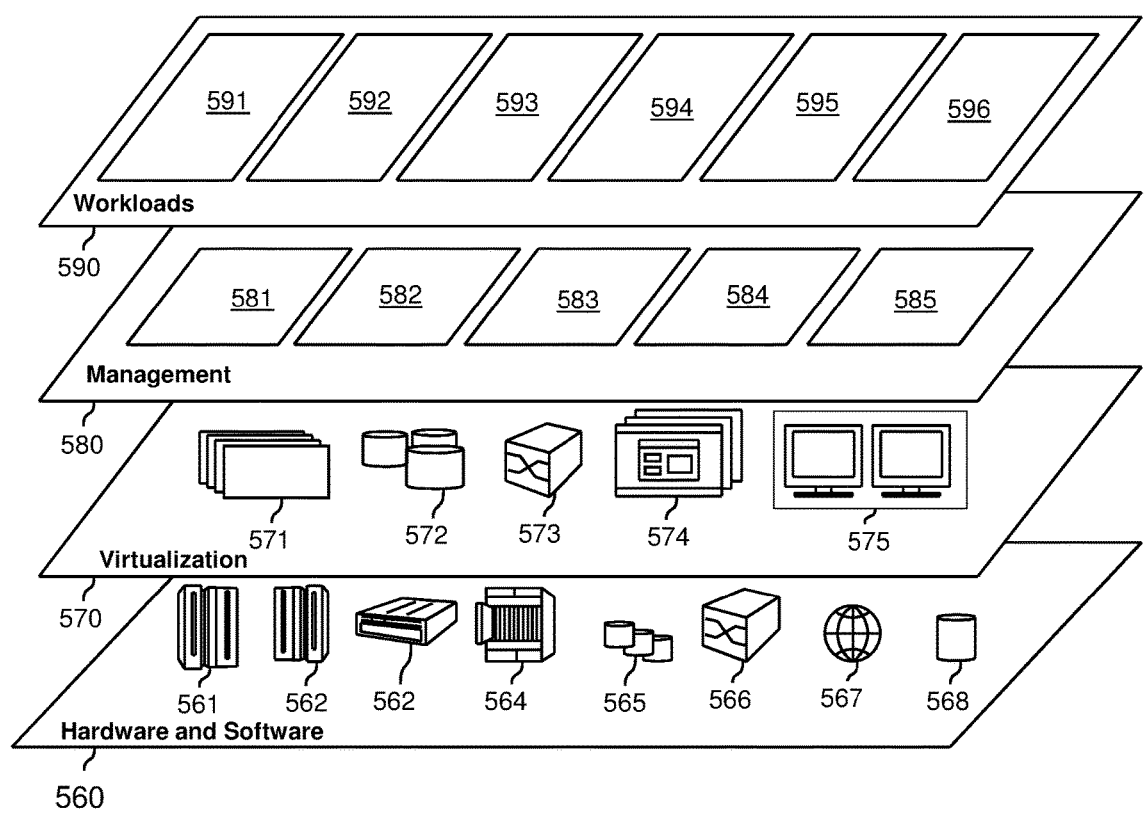
FIG. 8 depicts abstraction model layers according to one or more embodiments of the present invention.

Referring now to FIG. 8, a set of functional abstraction layers provided by cloud computing environment 450 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 560 includes hardware and software components. Examples of hardware components include: mainframes 561; RISC (Reduced Instruction Set Computer) architecture based servers 562; servers 563; blade servers 564; storage devices 565; and networks and networking components 566. In some embodiments, software components include network application server software 567 and database software 568.

Virtualization layer 570 provides an abstraction layer from which the following examples of virtual entities may be provided: virtual servers 571; virtual storage 572; virtual networks 573, including virtual private networks; virtual applications and operating systems 574; and virtual clients 575.

In one example, management layer 580 may provide the functions described below. Resource provisioning 581 provides dynamic procurement of computing resources and other resources that are utilized to perform tasks within the cloud computing environment. Metering and Pricing 582 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 583 provides access to the cloud computing environment for consumers and system administrators. Service level management 584 provides cloud computing resource allocation and management such that required service levels are met. Service Level Agreement (SLA) planning and fulfillment 585 provides pre-arrangement for, and procurement of, cloud computing resources for which a future requirement is anticipated in accordance with an SLA.

Workloads layer 590 provides examples of functionality for which the cloud computing environment may be utilized. Examples of workloads and functions which may be provided from this layer include: mapping and navigation 591; software development and lifecycle management 592; virtual classroom education delivery 593; data analytics processing 594; transaction processing 595; and a movement disorder management 596. The movement disorder management 596 may perform one or more methods that allow for evaluation of movement disorders using a UAV, such as but not limited to the methods described in reference to FIG. 5 for example.

Technical effects and benefits of one or more embodiments include the evaluation of motor characteristics related to movement disorders for a patient using an autonomously operated aerial vehicle.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    receiving, by a processor of an unmanned aerial vehicle (UAV), patient information for a patient to be evaluated;
    receiving, by the processor, a patient location
    using the processor of the UAV to guide the UAV to the patient location, the UAV having a patient evaluation feature and at least one contact sensor and at least one non-contact sensor operably coupled to the patient evaluation feature;
    positioning, by the processor, the UAV relative to the patient to measure a patient motor characteristic;
    measuring, by the processor, the patient motor characteristic with the at least one contact sensor and the at least one non-contact sensor;
    determining, by the processor, a movement disorder based at least in part on the measured patient motor characteristic; and
    transmitting, by the processor, a signal based on the detecting the movement disorder.

2. The method of claim 1, wherein the at least one sensor is an accelerometer.

3. The method of claim 2, further comprising integrating at least a portion of an accelerometer signal over a running interval, and transmitting the signal based on a magnitude of at least a portion of the integrated accelerometer signal exceeding a predetermined threshold.

4. The method of claim 1, further comprising instructing the patient to hold the patient evaluation feature with at least one hand prior to measuring the patient motor characteristic.

5. The method of claim 4, wherein the patient motor characteristic is an acceleration caused by a tremor in the at least one hand of the patient and the measurement is performed during a time period that the at least one hand of the touches the patient evaluation feature.

6. The method of claim 1, wherein the patient motor characteristic is selected from a group comprising a tremor, bradykinesia, rigidity, and postural instability.

7. The method of claim 1, further comprising moving the UAV from a first position to a second position after measuring the patient motor characteristic, and measuring a second patient motor characteristic in the second position.

8. The method of claim 1, further comprising moving the UAV from a first position to a second position during the measurement of the patient motor characteristic.

9. The method of claim 8, further comprising instructing the patient to point with a finger at the UAV prior to moving the UAV from the first position to the second position and instructing the patient to continue pointing the finger at the UAV during the movement from the first position to the second position.

10. The method of claim 9, further comprising recording a video image of the patient during the measurement of the patient motor characteristic.

11. The method of claim 1, wherein the measurement of the patient motor characteristic includes recording a video image of a patient's face, and the determining of the movement disorder includes using image analysis to determine a masked face.

12. A system comprising:
    a UAV having a patient evaluation feature and at least one contact sensor and at least one non-contact sensor operably coupled to the patient evaluation feature;
    a memory; and
    one or more processors communicatively coupled to the memory, the memory and one or more processors being operably coupled to the UAV, wherein the one or more processors are configured to execute operations comprising:
    defining a patient and a patient location;
    deploying the UAV to the location of the patient;
    positioning the UAV relative to the patient to measure a patient motor characteristic;
    measuring the patient motor characteristic with the at least one contact sensor and at least one non-contact sensor;
    determining a movement disorder based at least in part on the measured patient motor characteristic; and
    transmitting a signal based on the detecting the movement disorder.

13. The system of claim 12, wherein the at least one sensor is an accelerometer.

14. The system of claim 13, wherein the operations further comprise integrating at least a portion of an accelerometer signal over a running interval, and transmitting the signal based on a magnitude of at least a portion of the integrated accelerometer signal exceeding a predetermined threshold.

15. The system of claim 12, wherein the operations further comprise moving the UAV from a first position to a second position after measuring the patient motor characteristic, and measuring a second patient motor characteristic in the second position.

16. The system of claim 12, wherein the operations further comprise moving the UAV from a first position to a second position during the measurement of the patient motor characteristic.

17. The system of claim 16 wherein the operations further comprise instructing the patient to point with a finger at the UAV prior to moving the UAV from the first position to the second position and instructing the patient to continue pointing the finger at the UAV during the movement from the first position to the second position.

18. The system of claim 17 wherein the operations further comprise recording a video image of the patient during the measurement of the patient motor characteristic.

19. The system of claim 12 further comprising instructing the patient to hold the patient evaluation feature with at least one hand prior to measurement of the patient motor characteristic, wherein the patient motor characteristic is an acceleration caused by a tremor in the at least one hand of the patient during a time period that the at least one hand touches to patient evaluation feature.

20. A computer program product for a evaluating a patient for a movement disorder, the computer program product comprising a non-transitory computer readable storage medium having program instructions embodied therewith, the program instructions executable by a processor to cause the processor to perform a method comprising:
- receiving by an unmanned aerial vehicle (UAV), patient information for a patient to be evaluated;
- receiving a patient location
- traveling to the location of the patient, the UAV having a patient evaluation feature and at least one contact sensor and at least one non-contact sensor operably coupled to the patient evaluation feature;
- positioning the UAV relative to the patient to measure a patient motor characteristic;
- measuring the patient motor characteristic with the at least one contact sensor and at least one non-contact sensor;
- determining the movement disorder based at least in part on the measured patient motor characteristic; and
- transmitting a signal based on the detecting the movement disorder.

\* \* \* \* \*